(12) United States Patent
Knight

(10) Patent No.: US 8,313,438 B2
(45) Date of Patent: *Nov. 20, 2012

(54) INTEGRATED BIAS CIRCUITRY FOR ULTRASOUND IMAGING DEVICES CONFIGURED TO IMAGE THE INTERIOR OF A LIVING BEING

(75) Inventor: Jon M. Knight, Pleasanton, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/108,661

(22) Filed: May 16, 2011

(65) Prior Publication Data

US 2011/0218442 A1 Sep. 8, 2011

Related U.S. Application Data

(63) Continuation of application No. 10/966,594, filed on Oct. 14, 2004, now Pat. No. 7,967,754.

(51) Int. Cl.
*A61B 8/14* (2006.01)
*A61B 8/00* (2006.01)
(52) U.S. Cl. .................. 600/459; 600/443; 600/467
(58) Field of Classification Search .............. 600/443, 600/459, 467; 367/138, 153
See application file for complete search history.

(56) References Cited

U.S. PATENT DOCUMENTS

| | | |
|---|---|---|
| 4,852,577 A | 8/1989 | Smith et al. |
| 4,917,097 A | 4/1990 | Proudian et al. |
| 5,097,709 A | 3/1992 | Masuzawa et al. |
| 5,109,857 A | 5/1992 | Roundhill et al. |
| 5,187,687 A | 2/1993 | Burckhardt et al. |
| 5,195,519 A | 3/1993 | Angelsen |
| 5,373,849 A | 12/1994 | Maroney et al. |
| 5,671,747 A | 9/1997 | Connor |
| 5,876,345 A | 3/1999 | Eaton et al. |
| 5,913,823 A | 6/1999 | Hedberg et al. |

(Continued)

FOREIGN PATENT DOCUMENTS

GB 2368123 4/2002

OTHER PUBLICATIONS

Percin, G. et al., "Piezoelectrically Actuated Flextensional Micromachined Ulstrasound Transducers," Ultrasonics, vol. 40, No. 1-8, May 2002, pp. 441-448.

(Continued)

*Primary Examiner* — Michael Rozanski
(74) *Attorney, Agent, or Firm* — Frommer Lawrence & Haug LLP; Bruce E. Black

(57) ABSTRACT

The systems and methods described herein allow for the application of a bias voltage to one or more transducers implemented within a medical ultrasound imaging system. Bias circuitry is placed within an imaging device and used to apply a DC bias to one or more transducers requiring a DC bias to operate. The one or more transducers can be fabricated in a semiconductor manufacturing process and integrated with the bias circuitry on a common semiconductor substrate. Also provided is a method for operating the one or more transducers and bias circuitry using a communication channel having two signal lines.

20 Claims, 4 Drawing Sheets

U.S. PATENT DOCUMENTS

| | | | |
|---|---|---|---|
| 5,947,905 | A | 9/1999 | Hadjicostis |
| 5,964,709 | A | 10/1999 | Chiang et al. |
| 5,980,457 | A | 11/1999 | Averkiou |
| 6,083,164 | A | 7/2000 | Oppelt et al. |
| 6,241,676 | B1 | 6/2001 | Savord |
| 6,251,074 | B1 | 6/2001 | Averkiou et al. |
| 6,254,542 | B1 | 7/2001 | Hamilton et al. |
| 6,328,696 | B1 | 12/2001 | Fraser |
| 6,328,697 | B1 | 12/2001 | Fraser |
| 6,359,367 | B1 | 3/2002 | Sumanaweera et al. |
| 6,443,901 | B1 | 9/2002 | Fraser |
| 6,497,660 | B1 | 12/2002 | Dillman et al. |
| 6,499,348 | B1 | 12/2002 | Mamayek |
| 6,540,677 | B1 | 4/2003 | Angelsen et al. |
| 6,558,330 | B1 | 5/2003 | Ayter et al. |
| 6,572,546 | B1 | 6/2003 | Bax et al. |
| 6,605,043 | B1 | 8/2003 | Dreschel et al. |
| 6,645,145 | B1 | 11/2003 | Dreschel et al. |
| 6,773,401 | B1 | 8/2004 | Dreschel et al. |
| 6,795,374 | B2 | 9/2004 | Barnes et al. |
| 6,896,657 | B2 | 5/2005 | Willis |
| 7,351,204 | B2 | 4/2008 | Amemiya |
| 7,967,754 | B2 | 6/2011 | Knight |
| 2001/0016688 | A1 | 8/2001 | Moore |
| 2002/0120195 | A1 | 8/2002 | Hossack et al. |
| 2003/0091200 | A1 | 5/2003 | Pompei |
| 2003/0097069 | A1 | 5/2003 | Avinash et al. |
| 2003/0149358 | A1 | 8/2003 | Maskil et al. |
| 2003/0204140 | A1 | 10/2003 | Ferek-Patric et al. |
| 2004/0015079 | A1 | 1/2004 | Berger et al. |
| 2004/0059218 | A1 | 3/2004 | Kanda |
| 2005/0054929 | A1 | 3/2005 | Angelsen et al. |

OTHER PUBLICATIONS

Percin, G. et al., "Piezoelectrically Actuated Flextensional Micromachined Ulstrasound Transducers—II: Fabrication and Experiments," IEEE Transaction on Ultrasonics Ferroelectrics & Frequency Control, vol. 49, No. 5, May 2002, pp. 585-595.

Percin, G. et al., "Piezoelectrically Actuated Flextensional Micromachined Ulstrasound Transducers—I: Theory," IEEE Transactions on Ultrasonics Ferroelectrics & Frequency Control, vol. 49, No. 5, May 2002, pp. 573-584.

Oralkan, O. et al., "CMUT Ring Arrays for Forward-Looking Intravascular Imaging," Ultrasonics Symposium, 2004 IEEE Montreal, Canada, Aug. 23-27, 2004, Piscataway, New Jersey, IEEE, Aug. 23, 2004, pp. 403-406.

Office Communication for U.S. Appl. No. 10/966,594 mailed Jun. 4, 2007.

Office Communication for U.S. Appl. No. 10/966,594 mailed Jul. 9, 2008.

Office Communication for U.S. Appl. No. 10/966,594 mailed May 25, 2010.

Office Communication for U.S. Appl. No. 10/966,594 mailed Aug. 30, 2010.

Office Communication for U.S. Appl. No. 10/966,594 mailed Oct. 27, 2010.

Office Communication for U.S. Appl. No. 10/966,594 mailed Feb. 15, 2011.

International Search Report and Written Opinion for International Patent Application No. PCT/US2005/036868 mailed Feb. 14, 2006.

INTEGRATED BIAS CIRCUITRY FOR ULTRASOUND IMAGING DEVICES CONFIGURED TO IMAGE THE INTERIOR OF A LIVING BEING

CROSS-REFERENCE TO RELATED APPLICATIONS

This patent application is a continuation of U.S. patent application Ser. No. 10/966,594 filed on Oct. 14, 2004, now U.S. Pat. No. 7,967,754, which is incorporated herein by reference.

FIELD OF THE INVENTION

The systems and methods relate generally to the use of bias circuitry for biasing an ultrasound imaging device in an intravascular ultrasound imaging system.

BACKGROUND INFORMATION

To generate an image using a medical ultrasound imaging system, such as an intravascular ultrasound (IVUS) or intracardiac echocardiography (ICE) imaging system, an ultrasound imaging device, typically including one or more transducers, is located on or within an intravascular device, such as a catheter and the like. The intravascular device is navigated into the body and the imaging device is used to image the desired body tissue. To do this, the transducer generates and transmits an ultrasound pulse into the body tissue. As this pulse strikes various layers of body tissue, echoes are reflected back to and received by the transducer. The transducer generates an electrical output signal representative of the strength of the received echo and outputs this signal to an image processing system. The image processing system processes the signal and uses it to form an image of the body tissue.

Conventionally, ultrasound transducers have been made of piezoelectric materials which require ceramic manufacturing technologies which are vastly different from those used to manufacture other components in an ultrasound imaging system, which are typically semiconductor-based. Piezoelectric transducers typically have a narrow bandwidth which limits the depth of tissue that can be imaged.

Recently, a new type of transducer has been developed capable of fabrication with semiconductor-based processing technologies. Capacitive micromachined ultrasonic transducers (CMUTs) were designed to answer a need to mass fabricate medical, ultrasound transducers using the very same semiconductor manufacturing processes used to fabricate the other parts of an external ultrasound imaging system. CMUTs are typically much smaller than piezoelectric transducers (on the order of 10 to 100 microns in size) and have a larger bandwidth.

A typical CMUT includes a drumhead structure suspended over a substrate in a manner to allow two-way conversion between a mechanical wave and an electrical signal through modulation of a capacitive charge on the drumhead. To deliver an ultrasound pulse, the capacitive charge on the drumhead, measured relative to a substrate electrode, is modulated by delivery of an electrical pulse to the drumhead. The delivery of this pulse causes the drumhead to vibrate and thereby transmit an ultrasound wave. Likewise, in the receiving mode, the impact of the echo on the drumhead modulates the capacitance and results in an electrical signal representative of the strength of the received echo.

CMUT devices are not currently used in IVUS imaging systems: One reason for this is because in order to operate, the CMUT needs a constant bias voltage that is carefully controlled so as to maintain high transducer sensitivity without short-circuiting the transducer's capacitance. Accordingly, there is a need for systems and methods for applying this bias voltage to CMUT devices in intravascular ultrasound imaging systems.

SUMMARY

The systems and methods described herein provide for an imaging system having bias circuitry for applying a bias voltage to one or more transducers. In one example embodiment, the imaging system includes an imaging device insertable into a living being and configured to image the interior of the living being. The imaging device includes an ultrasound transducer and bias circuitry electrically coupled with the transducer and configured to electrically bias the transducer. The imaging device can be coupled with a rotatable driveshaft and communicatively coupled with an image processing system. The image processing system can be configured to output a transducer drive signal to the transducer over a signal line located along the driveshaft and supply charge to the bias circuitry over the same signal line. Preferably, the transducer is CMUT capable of fabrication in a semiconductor-based manufacturing process. In one embodiment, the transducer is a CMUT and is integrated with the bias circuitry on a common semiconductor substrate. The bias circuitry can include a charge pump for accumulating the bias voltage and also charge limiting circuitry for controlling the bias voltage.

The systems and methods described herein also provide for an image processing system configured to operate an imaging device having bias circuitry. In one example embodiment, the image processing system can be configured to output a transducer drive signal during a first time period, receive a transducer output signal during a second time period and output a bias signal during a third time period. The transducer drive signal can be configured to cause a transducer within the imaging device to generate an ultrasound pulse. The transducer output signal is preferably representative of an echo received by the transducer. The bias signal can be configured to provide electrical charge to bias circuitry coupled with the transducer.

The systems and methods described herein also provide for a method of ultrasound imaging with an image processing system. In one example embodiment, the method includes outputting a transducer drive signal during a first time period, where the transducer drive signal is configured to cause a transducer to transmit an ultrasound pulse. The method also includes receiving a transducer output signal during a second time period following the first time period, where the transducer output signal is representative of an echo received by the transducer, and outputting a bias signal during a third time period following the second time period, where the bias signal is configured to provide charge to bias circuitry. In another example embodiment, the method can include outputting a second bias signal during a fourth time period prior to the first time period, where the second bias signal output during the fourth time period is configured to initialize the bias circuitry. The fourth time period can also be longer than the third time period.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. It is also intended that the invention is not limited to require the details of the example embodiments.

BRIEF DESCRIPTION OF THE FIGURES

The details of the invention, including fabrication, structure and operation, may be gleaned in part by study of the accompanying figures, in which like reference numerals refer to like segments.

DETAILED DESCRIPTION

Figure 1:
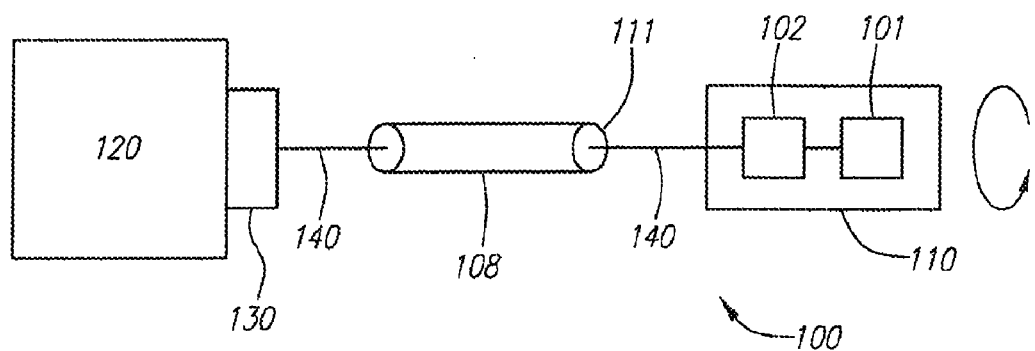
FIG. 1 is a schematic view depicting an example embodiment of an IVUS imaging system.

The systems and methods described herein allow the application of a bias voltage to one or more transducers implemented within an imaging system. FIG. 1 depicts one example embodiment of an imaging system 100 having bias circuitry 102. Preferably, the imaging system 100 is an IVUS imaging system. Here, an intravascular medical device 104, such as a catheter and the like, is communicatively coupled with an image processing system 106. Catheter 104 is preferably configured to image the interior of a living being, such as a body chamber or body lumen and the like. Catheter 104 preferably includes a rotatable driveshaft 108 with an imaging device 110 coupled thereto. In this embodiment, the imaging device 110 is mounted on the distal end 111 of the driveshaft 108. The catheter 104 also preferably includes an elongate outer sheath (not shown) having an inner lumen for slidably receiving the driveshaft 108 and imaging device 110.

To perform an imaging procedure of, for example, a blood vessel, the catheter 104 can be inserted into the blood vessel and navigated into proximity with the desired imaging location. Once in position, the driveshaft 108 is rotated and the imaging device 110 is used to image the blood vessel by continuously transmitting ultrasound pulses and receiving echoes generated as the ultrasound pulse travels through the vessel tissue. Imaging device 110 outputs an output signal representative of the strength of the received echo over communication channel 140 to image processing system 120, where the signal can be processed and formed into an image of the blood vessel and surrounding body tissue.

A coupling device 130 can be used to couple the stationary image processing system 120 with the rotatable driveshaft 108. In one embodiment, coupling device 130 is an inductive coupling configured to transfer communication signals, such as the imaging device output signal and the transducer drive signal, between image processing system 120 and communication channel 140.

In this embodiment, the imaging device 110 includes one or more transducers 101 requiring a bias voltage for operation, such as a CMUT and the like. The imaging device 101 can operate with a single transducer 101 or with a transducer array having multiple transducers 101. Each transducer 101 is preferably fabricated using a semiconductor-based manufacturing technique, although any fabrication technique can be used. For ease of discussion, the transducer 101 will be described herein as a CMUT; however, one of skill in the art will readily recognize that the systems and methods described herein can be used with any transducer 101 requiring a bias voltage, such as other types of micromachined ultrasound transducers (MUTs) and the like. Accordingly, the systems and methods are not limited solely to the use of CMUT devices.

Figure 2:
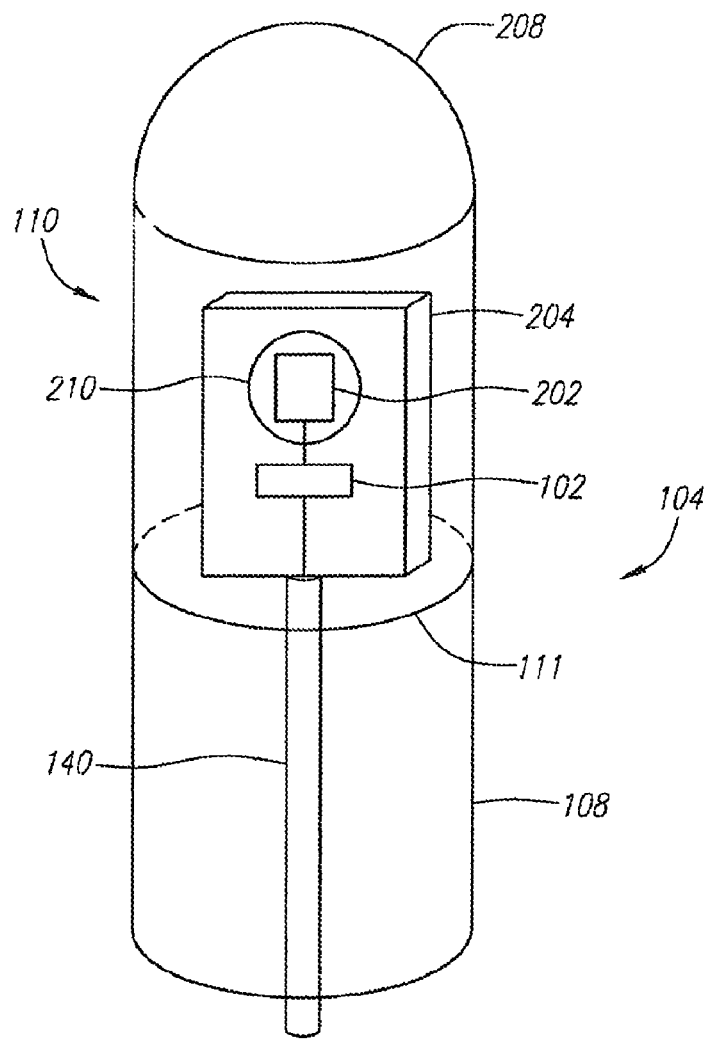
FIG. 2 is a perspective view depicting another example embodiment of an IVUS imaging system.

The imaging device 110 also includes bias circuitry 102 for applying a DC voltage bias to the CMUT 101. Preferably, the CMUT 101 and bias circuitry 102 are integrated together. FIG. 2 is a perspective view depicting a CMUT array 202 integrated with bias circuitry 102 on a common semiconductor substrate 204, such as Silicon, Gallium Arsenide (GaAs) and the like. The integrated CMUT array 202 and bias circuitry 102 are located within housing 208 and mounted on the distal end 111 of driveshaft 108. Housing 208 preferably includes an imaging window 210, which can be either an open portion of the housing 208 or a window formed from a material that does not significantly impede the transmission or reception of ultrasound signals. Although not depicted here, the integrated CMUT array 202 and bias circuitry 102 can be packaged using any desired packaging technique in order to provide protection, ease of mounting within housing 208 or for any other desired purpose.

As mentioned above, CMUTs 101 are typically fabricated using semiconductor-based manufacturing processes on a semiconductor substrate 204. Preferably, the bias circuitry 102 is integrally fabricated on the same substrate 204 as the CMUT 101. CMUT 101 and bias circuitry 102 can be fabricated using the same process flow or in different process flows. In embodiments having a CMUT array 202, bias circuitry 101 can be configured to bias each individual CMUT 101 in the array 202 or multiple bias circuits 101 can be provided to bias each CMUT separately. The integration of bias circuitry 102 with CMUT 101 allows for improved performance of the imaging device 110 while at the same time making fabrication of the imaging device easier and less costly. Although integration of CMUT 101 and bias circuitry 102 on common substrate 204 is preferred, it should be understood that the systems and methods described herein are not limited to such. For instance, CMUT 101 and bias circuitry 102 can be fabricated as discrete components and packaged together, or fabricated and packaged discretely. Furthermore, CMUT 101 and bias circuitry 102 are not required to be housed together within housing 208, and in fact can be positioned in any desired location within catheter 104.

Figure 3A:
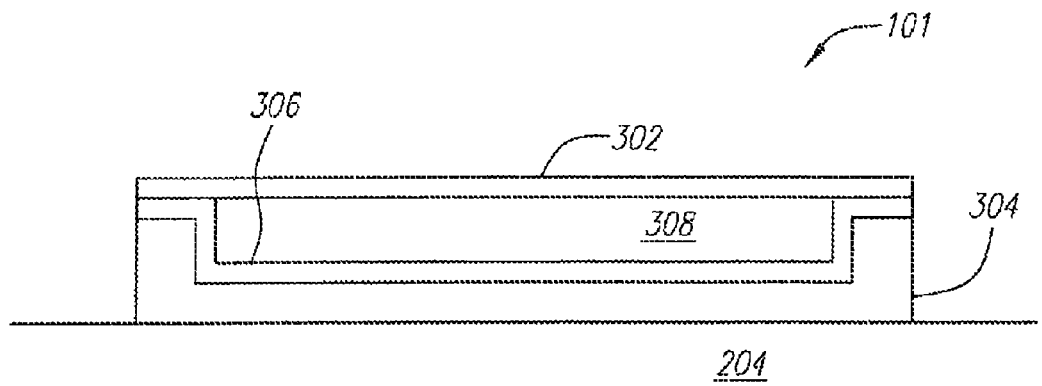
FIGS. 3A-B are cross-sectional views depicting an example embodiment of a CMUT.
Figure 3B:
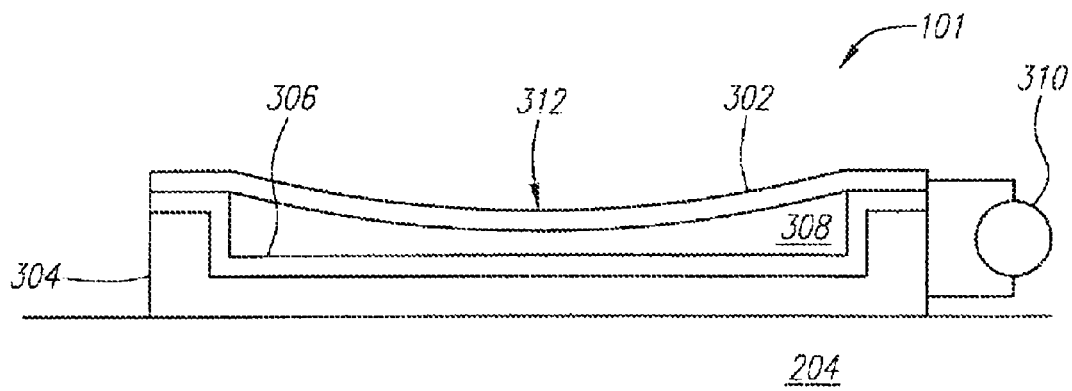

FIGS. 3A-B are cross-sectional views depicting an example embodiment of a CMUT 101. FIG. 3A depicts an unbiased CMUT 101 having a flexible upper electrode 302 suspended over a lower electrode 304 both of which are fabricated on substrate 204. The flexible upper electrode 302 is also referred to in some contexts as a "drumhead." Located between electrodes 302 and 304 is an insulator layer 306, composed of an insulating material such as silicon oxide or the like. Preferably, upper electrode 302 and lower electrode 304 are separated by a gap 308. Upper electrode 302 can completely encase gap 308 on all sides, in which case gap 308 is preferably a vacuum.

FIG. 3B depicts CMUT 101 after a DC bias voltage 310 is applied across electrodes 302 and 304. DC bias voltage 310 builds a capacitive charge on the electrodes 302 and 304 causing upper electrode 302 to flex, or deflect, downwards towards lower electrode 304 in direction 312. The application of a drive signal, such as an electrical pulse or an AC signal, to the biased CMUT 101 modulates the degree of deflection of upper electrode 302 causing the generation of an ultrasound pulse, which can be used to image body tissue. Conversely, when an ultrasound pulse, such as a received echo, impacts the biased CMUT 101, an electrical pulse corresponding to the strength of the received echo is generated. In this manner, CMUT 101 can be used to transmit and receive ultrasound signals in IVUS imaging system 100.

The actual DC bias voltage 310 and drive signal levels are dependent on the needs of the application and the characteristics of each CMUT 101. In general, a larger DC bias voltage 310 will translate into the generation of a stronger ultrasound pulse. In addition, the bias voltage 310 can also be a factor in determining the frequency of the generated ultrasound pulse. In some applications, the DC bias voltage 310 can be approximately 100-150 volts, while the drive signal level can be 75 volts or more. It should be understood that these values are provided solely as examples and any signal levels can be used as desired.

The design and fabrication of CMUT devices is discussed further in Percin, G. and B. Khuri-Yakub, Piezoelectrically actuated flextensional micromachined ultrasound transducers, Ultrasonics, 2002. 40(1-8): p. 441-8, Percin, G. and B. Khuri-Yakub, *Piezoelectrically actuated flextensional micromachined ultrasound transducers-II: fabrication and experiments*, IEEE Trans Ultrason Ferroelectr Freq Control, 2002. 49(5): p. 585-95 and Percin, G. and B. Khuri-Yakub, *Piezoelectrically actuated flextensional micromachined ultrasound transducers-I: theory*, IEEE Trans Ultrason Ferroelectr Freq Control, 2002. 49(5): p. 573-84, each of which is fully incorporated by reference herein.

Figure 4:
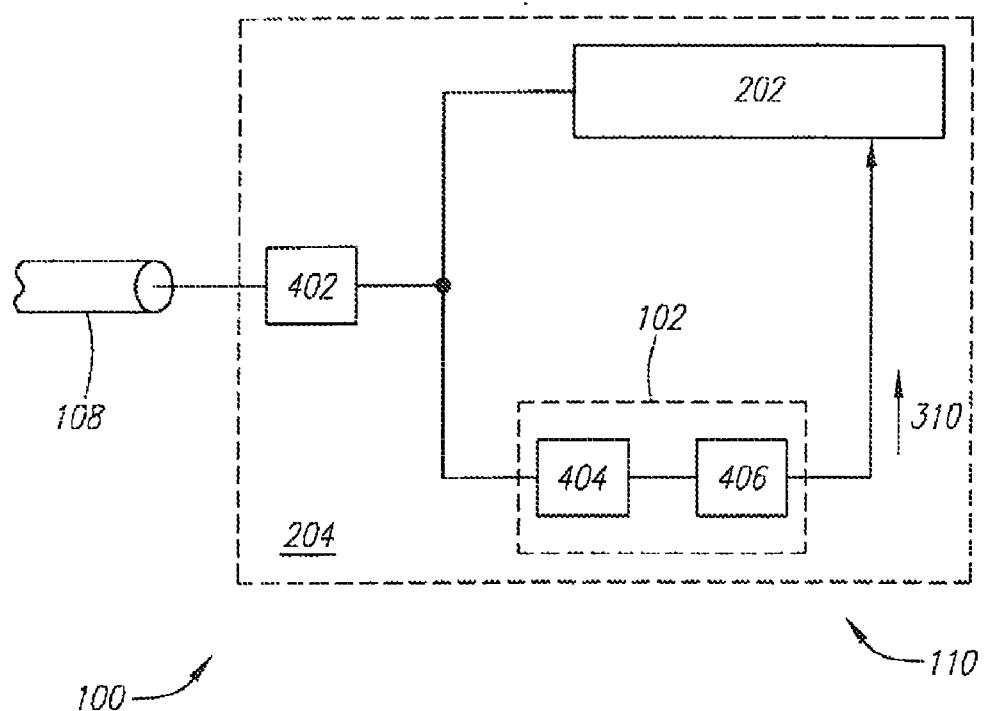
FIG. 4 is a block diagram depicting an example embodiment of an IVUS imaging device.

FIG. 4 depicts another example embodiment of imaging device 110. In this embodiment, imaging device 110 includes CMUT array 202, bias circuitry 102 and rectification circuit 402, all of which are preferably integrated on common substrate 204. Bias circuitry 102 includes a signal blocking circuit 404 and a charge pump 406 configured to apply the DC bias voltage 310 to the array 202. A bias signal is preferably transmitted along communication channel 140 to supply charge to charge pump 404 and generate the DC bias voltage level 310 necessary to properly bias the CMUTs 101 within array 202. The design and implementation of charge pumps are well known to those of skill in the art and any type of charge pump can be used. The charge pump preferably includes a charge storage unit, such as a switched capacitor bank and the like. Furthermore, DC bias circuitry 102 can be any circuitry configured to control and apply a DC bids voltage including, but not limited to, a charge pump 404.

In embodiments where coupling device 130 uses an inductive or other non-physical electrical coupling to transfer AC signals between image processing system 120 and imaging device 110, the bias signal is preferably a series of DC pulses that appear as an AC signal to the coupling device 130. In embodiments where coupling device 130 uses a physical coupling, such as a brush/contact combination, the bias signal can be a pure DC signal if desired.

Rectification circuit 402 can be used to isolate the charge built up within imaging device 110. Because system 100 can be used primarily for medical imaging within living beings, rectification circuit 402 guards against the risk of electrical shock or other hazards to the patient or the circuitry of system 100. Specifically, rectification 402 can be used to block or prevent signals, such as the charge in charge pump 406 or array 202, from propagating onto communication channel 140. Any type of rectification circuitry can be used, such as one or more diodes and the like. Signal blocking circuit 404 can be used to block the CMUT drive signal from propagating to charge pump 406. One of skill in the art will readily recognize that FIG. 4 depicts one of many possible different circuit layouts for imaging device 110 and, accordingly, the systems and methods described herein are not limited to any one layout or circuit design.

Communication channel 140 can include any number of signal lines or transmission lines as needed. For example, communication channel can include a ground signal line, a CMUT drive signal line and a bias circuitry bias signal line. However, because system 100 is preferably used for intravascular applications, the width of catheter 104 can be a limiting factor preventing advancement through narrow vasculature. Thus, because each additional signal line generally adds width to the driveshaft 108, even if the driveshaft 108 itself is used as a signal line, the number of signal lines used in communication channel 140 is preferably minimized. Typical IVUS imaging systems use a communication channel 140 that includes two signal lines which can be used to transfer single-ended or differential signals.

Figure 5:
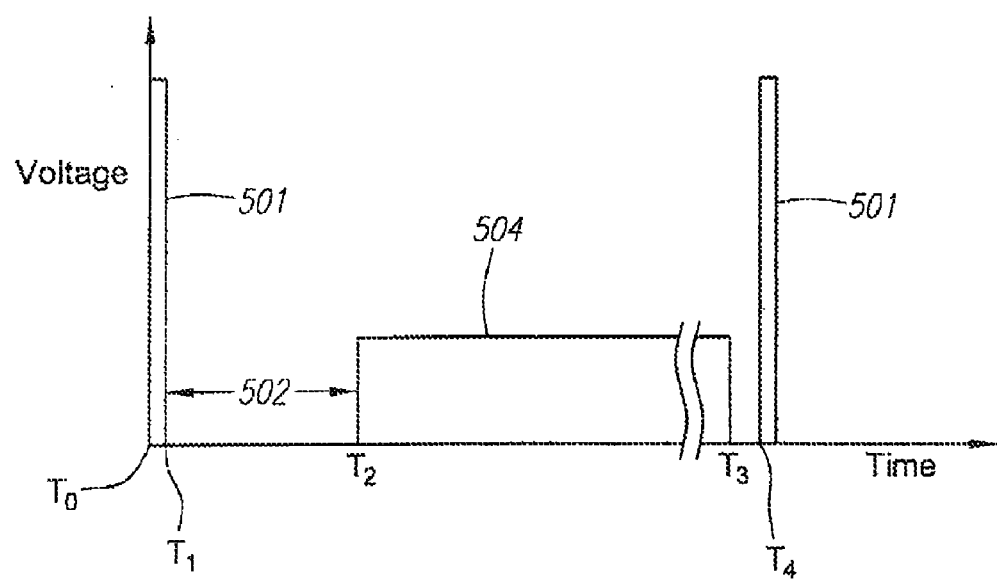
FIG. 5 is a timing diagram depicting example output signals from an image processing system.

In order to use two signal lines to transfer the transducer drive signal, the bias signal and the transducer output signal, the systems and methods described herein use a segmented timing regime. FIG. 5 is a timing diagram depicting the signals output from image processing system 120 according to one example embodiment of the segmented timing regime. In this embodiment, imaging device 110 is rotated to image a cross-section of the body lumen. The transmission of an ultrasound pulse followed by the reception of the resulting echo signals is referred to herein as an imaging cycle. System 100 can be configured to perform a predetermined number of imaging cycles for every rotation, with each imaging cycle being performed at a separate angular location, or range of angular locations. For instance, in one embodiment, imaging device 110 performs 360 imaging cycles in each rotation, with one imaging cycle being performed at an angular location located one degree apart.

Preferably, imaging device 110 is rotated at a rate such that the time required to perform an imaging cycle is less than the time required to rotate the imaging device 110 from one angular location to the next. For example, in FIG. 5, at time $T_0$ the imaging device 110 is at a first angular location and at time $T_4$ the imaging device 110 has been rotated to a second angular position. The imaging cycle for the first angular location occurs between times $T_0$ and $T_2$. More specifically, the CMUT drive signal 502 is transmitted from image processing system 120 to the array 202 from time $T_0$ to time $T_1$ in order to cause each individual CMUT 101 to transmit an ultrasound pulse. From time $T_1$ to time $T_2$, image processing system 120 is in a receiving period 502 awaiting any output signals generated by the array 202 in response to received echoes. This leaves the remaining time from $T_2$ to $T_4$ unused in any imaging cycle.

During the time from $T_2$ to $T_3$, the image processing system 120 preferably transmits the bias signal 504 to bias circuitry 102. At time $T_4$, the image processing system 120 transmits another drive signal 501 to initiate the imaging cycle at the next angular location. In one example embodiment, the time period from $T_0$ to $T_4$ is 130 microseconds, with the time period from $T_0$ to $T_1$ being approximately 50 nanoseconds, the time period from $T_1$ to $T_2$ being approximately 20 microseconds and the time period from $T_2$ to $T_3$ being approximately 100 microseconds. These times are included as examples only and in no way limit the systems and methods described herein.

Bias circuitry 102 can use the bias signal to generate the required DC bias voltage 310. The amplitude of the bias signal 504 is preferably lower than the CMUT 101 excitement threshold where the CMUT 101 produces an ultrasound pulse. In some applications, small ultrasound pulses may be tolerable if, for instance, the small ultrasound pulse does not interfere with the subsequent imaging cycle. The term "excitement threshold" as used herein, refers to the signal level which causes one or more transducers to generate ultrasound pulses at a level sufficient to interfere with an imaging cycle. In one embodiment, the excitement threshold can be 75 volts and the bias signal 504 is maintained at 70 volts, while the drive signal 501 is 125 volts. These values are solely for example and in no way limit the systems and methods described herein. As mentioned above, the bias signal can be a series of DC pulses instead of a continuous DC pulse in order to propagate through coupling device 130, if needed. Also, it should be understood that any waveforms can be used for drive signal 501 and bias signal 504.

The generation of bias signal 504 and drive signal 501, as well as the proper timing for doing so, can be controlled by the image processing system 120. Preferably, the bias circuitry 102 is configured to limit the charge build up so that the bias signal 504 does not cause bias circuitry 102 to apply a DC bias voltage 310 that is too high. This can be performed through charge limiting circuitry well known to those of skill in the art. Also, in certain applications, multiple charging cycles may be needed before bias circuitry 102 can apply the proper. DC bias voltage 310. Alternatively, in another embodiment the image processing system 120 can be configured to output the bias signal prior to the commencement of imaging in order to charge up, or initialize, the bias circuitry 102. In this embodiment, the length of the initialization period can be as long as needed to charge the bias circuitry 102. Preferably, the bias circuitry 102 is designed to be low leakage so that once the proper DC bias voltage 310 is reached, minimal subsequent charging is needed.

Figure 6:
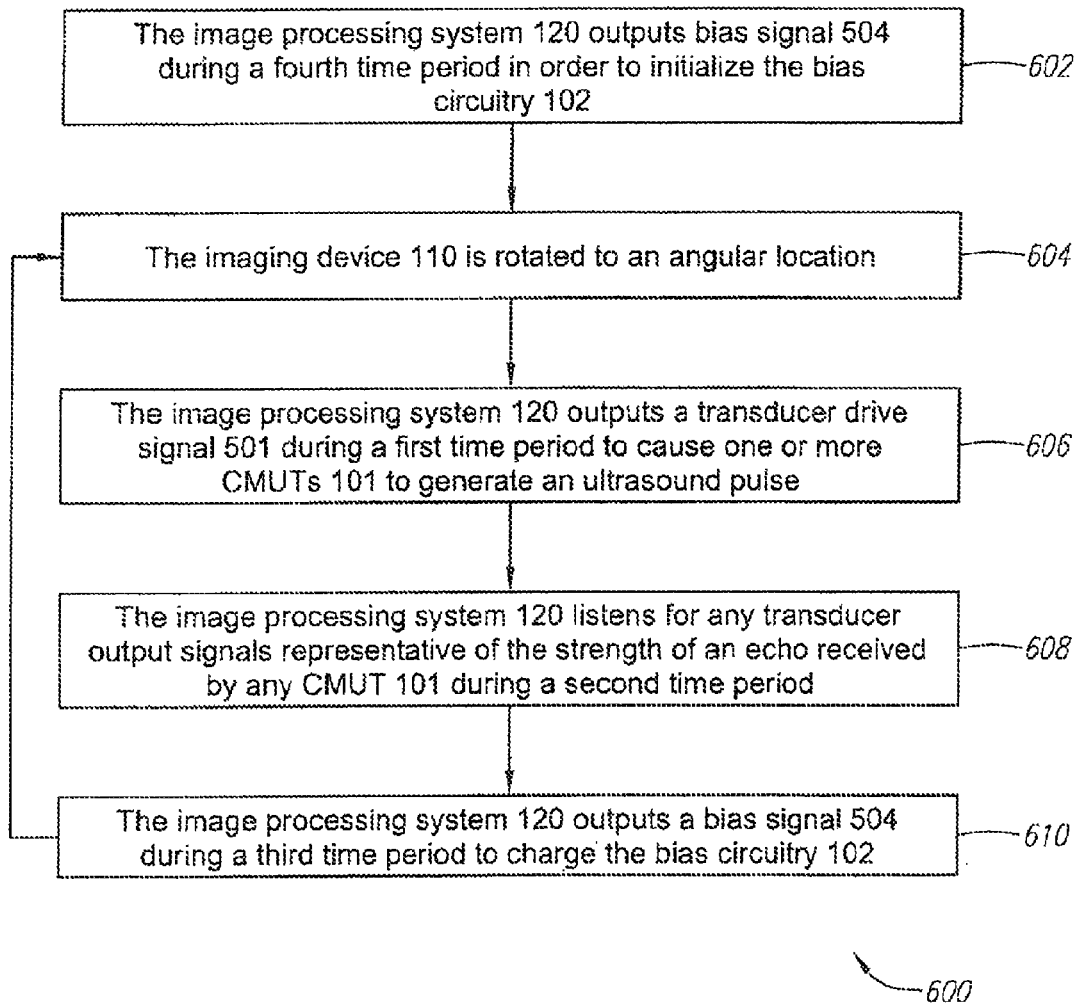
FIG. 6 is a flow diagram depicting a method of operating an imaging device with an image processing system.

FIG. 6 is a flow chart depicting a method 600 of operating the imaging device 110 with an image processing system 120 in an embodiment where communication channel 140 has only two signal lines available. At 604, the imaging device 110 is rotated to a first angular location. At 606, the image processing system 120 outputs a transducer drive signal 501 during a first time period to cause one or more CMUTs 101 to generate an ultrasound pulse. At 608, the image processing system 120 listens for any transducer output signals representative of the strength of an echo received by any CMUT 101 during a second time period. At 610, the image processing system 120 outputs a bias signal 504 during a third time period to charge the bias circuitry 102.

In addition, method 600 can also include an optional initialization process, referenced as 602, where the image processing system 120 can output bias signal 504 during a fourth time period, preferably in order to initialize the bias circuitry 102. Then, the method returns to step 604 and rotates to the next angular position and repeats steps 606-610. This process continues until imaging at all of the desired angular locations has taken place. The rotation of imaging device is preferably continuous but performed at such a rate where the rotation that occurs during the imaging cycle is negligible for the needs of the application.

In the foregoing specification, the invention has been described with to specific embodiments thereof. It will, however, be evident that various modifications and changes may be made thereto without departing from the broader spirit and scope of the invention. For example, each feature of one embodiment can be mixed and matched with other features shown in other embodiments, and the sequence of steps shown in a flowchart may be changed. Features and processes known to those of ordinary skill may similarly be incorporated as desired. Additionally and obviously, features may be added or subtracted as desired. Accordingly, the invention is not to be restricted except in light of the attached claims and their equivalents.

What is claimed and desired to be protected by Letters Patent of the United States is:

1. A medical imaging system, comprising:
    an imaging device configured and arranged to be insertable into an intravascular portion of a living being and to image the interior of the living being, the imaging device comprising:
      an ultrasound transducer; and
      bias circuitry electrically coupled with the transducer and configured and arranged to electrically bias the transducer;
    a driveshaft coupled to the imaging device and configured and arranged for rotating the imaging device;
    a signal line located along the driveshaft and coupled to both the ultrasound transducer and the bias circuitry and configured and arranged for delivery of both a transducer drive signal to the transducer and a charge to the bias circuitry;
    an image processing system configured and arranged to provide the transducer drive signal and the charge for the bias circuitry; and
    a coupling device configured and arranged to inductively couple the signal line to the image processing system, wherein the image processing system is configured and arranged to provide the charge for the bias circuitry using a signal which appears as an AC signal to the coupling device.

2. The system of claim 1, wherein the transducer includes a capacitive micromachined ultrasound transducer (CMUT).

3. The system of claim 2, wherein the bias circuitry is integrated with the CMUT on a common semiconductor substrate.

4. The system of claim 1, wherein the transducer is one of a plurality of transducers within a transducer array.

5. The system of claim 1, wherein the bias circuitry comprises a charge pump.

6. The system of claim 1, wherein the imaging device comprises rectification circuitry.

7. The system of claim 1, wherein the bias circuitry is configured and arranged to control a bias voltage.

8. The system of claim 7, wherein the bias circuitry comprises charge limiting circuitry configured to control the bias voltage.

9. The system of claim 1, wherein the image processing system is configured and arranged to provide the charge for the bias circuitry using a series of DC pulses provided in a single imaging cycle.

10. The system of claim 1, wherein the image processing system is configured and arranged to output the transducer drive signal to the transducer via the signal line during a first time period, receive an echo signal during a second time period, and output the charge for the bias circuitry via the signal line during a third time period, wherein the second time period is after the first time period and the third time period is after the second time period and wherein the first time period, the second time period, and the third time period are in a single imaging cycle.

11. The system of claim 10, wherein the bias circuitry comprises a charge pump and the amplitude of the bias signal is below an excitement threshold for the transducer.

12. The system of claim 10, wherein the image processing system is further configured to output a bias signal during a fourth time period, longer than the third time period and prior to the first time period.

13. The system of claim 12, wherein the bias circuitry comprises a charge pump and the bias signal output during the fourth time period is configured to initialize the charge pump.

14. A intravascular ultrasound imaging system, comprising:
- an imaging device configured and arranged to be insertable into an intravascular portion of a living being and to image the interior of the living being, the imaging device comprising:
  - an ultrasound transducer; and
  - bias circuitry electrically coupled with the transducer and configured and arranged to electrically bias the transducer;
- a driveshaft coupled to the imaging device and configured and arranged for rotating the imaging device;
- an image processing system configured and arranged to output a transducer drive signal during a first time period, receive an echo signal during a second time period and output a bias signal during a third time period, wherein the second time period is after the first time period and the third time period is after the second time period and wherein the first time period, the second time period, and the third time period are in a single imaging cycle;
- a signal line located along the driveshaft and coupled to the image processing system, the ultrasound transducer, and the bias circuitry and configured and arranged for transmission of the transducer drive signal, the echo signal, and the bias signal;
- wherein the transducer drive signal is configured and arranged to cause a transducer to generate an ultrasound pulse, the echo signal is representative of an echo received by the transducer and the bias signal is configured and arranged to provide electrical charge to the bias circuitry.

15. The system of claim 14, wherein the bias signal is a DC signal.

16. The system of claim 14, wherein the bias signal is a series of DC pulses.

17. The system of claim 14, wherein the image processing system is further configured to output the bias signal during a fourth time period, longer than the third time period and prior to the first time period.

18. The system of claim 17, wherein the bias circuitry comprises a charge pump and where the bias signal output during the fourth time period is configured to initialize the charge pump.

19. The system of claim 14, wherein the transducer comprises a capacitive micromachined ultrasound transducer (CMUT) and the bias circuitry is integrated with the CMUT on a common semiconductor substrate.

20. The system of claim 14, wherein the bias circuitry comprises charge limiting circuitry configured to control a bias voltage.

* * * * *